(12) United States Patent
Kim

(10) Patent No.: US 10,646,645 B2
(45) Date of Patent: May 12, 2020

(54) MEDICAL INJECTION DEVICE

(71) Applicant: DONGKOO BIO & PHARMA CO., LTD., Seoul (KR)

(72) Inventor: Jun-Woo Kim, Daegu (KR)

(73) Assignee: DONGKOO BIO & PHARMA CO., LTD., Seoul (KR)

( * ) Notice: Subject to any disclaimer, the term of this patent is extended or adjusted under 35 U.S.C. 154(b) by 0 days.

(21) Appl. No.: 16/304,031

(22) PCT Filed: Mar. 22, 2017

(86) PCT No.: PCT/KR2017/003039
§ 371 (c)(1),
(2) Date: Nov. 21, 2018

(87) PCT Pub. No.: WO2017/204448
PCT Pub. Date: Nov. 30, 2017

(65) Prior Publication Data
US 2019/0365988 A1  Dec. 5, 2019

(30) Foreign Application Priority Data

May 25, 2016 (KR) .................. 10-2016-0063940

(51) Int. Cl.
*A61M 5/168* (2006.01)
*A61J 1/20* (2006.01)
*A61M 5/165* (2006.01)

(52) U.S. Cl.
CPC .............. *A61M 5/168* (2013.01); *A61J 1/20* (2013.01); *A61M 5/165* (2013.01); *A61M 2205/3331* (2013.01)

(58) Field of Classification Search
CPC .... A61M 5/168; A61M 5/14; A61M 5/16804; A61M 5/16813; A61M 5/16822;
(Continued)

(56) References Cited

U.S. PATENT DOCUMENTS 4,055,176 A * 10/1977 Lundquist ............... A61M 5/40
604/127
4,256,104 A * 3/1981 Muetterties ......... A61M 5/1408
137/113
(Continued)

FOREIGN PATENT DOCUMENTS

JP    2000-509620 A    8/2000
JP    2005-532105 A   10/2005
(Continued)

*Primary Examiner* — Kevin C Sirmons
*Assistant Examiner* — Alexandra Lalonde
(74) *Attorney, Agent, or Firm* — Medler Ferro Woodhouse Mills PLLC

(57) ABSTRACT

The present invention relates to a medical injection device for preventing a target substance contained in an injection solution from being lost when the target substance is not settled or floated, and for evenly agitating the injection solution to be safely injected. A medical injection device according to the present invention includes a container having an agitation means and a vibration sensing ball, an injection solution filter, an injection solution level controller, a bellows connector, and a guide tube.

21 Claims, 16 Drawing Sheets

(58) Field of Classification Search
CPC .. A61M 5/165; A61M 5/1411; A61M 5/1414;
A61M 5/36; A61M 5/365; A61M
5/16877; A61M 5/16881; A61M 5/00;
A61M 5/162; A61M 5/40; A61M 5/1415;
A61M 5/1417; A61M 5/1418; A61M
2005/1403; A61M 2005/1401; A61M
2005/1402; A61M 2005/1652; A61M
2005/1655; A61M 2005/1657; A61M
2005/1623; A61M 2205/3331; A61M
2205/3334; A61M 2039/2473; A61M
2039/248; A61M 2039/2493; A61M
39/10; A61J 1/14; A61J 1/2003; A61J
1/2068; A61J 1/2072; A61J 1/2075; A61J
1/2079; A61J 1/2082; A61J 1/2086; B01F
5/00; B01F 11/00; B01F 11/006; B01F
11/0062; B01F 11/008; B01F 11/0068;
B01F 11/0085; B01F 11/0094; B01F
13/005; B01F 13/0052; B01F 13/0055;
B01F 13/0054; B01F 13/0057; B01F
15/0085; B01F 15/00512
See application file for complete search history.

(56) References Cited

U.S. PATENT DOCUMENTS

| | | | | |
|---|---|---|---|---|
| 4,335,717 A | * | 6/1982 | Bujan | A61M 5/1408 604/34 |
| 8,177,740 B1 | * | 5/2012 | McGlothlin | A61M 5/152 604/82 |
| 2006/0122576 A1 | * | 6/2006 | Raja | A61M 3/0258 604/890.1 |
| 2008/0097315 A1 | * | 4/2008 | Miner | A61M 5/1411 604/122 |
| 2017/0115156 A1 | * | 4/2017 | Uber, III | A61M 5/40 |

FOREIGN PATENT DOCUMENTS

| | | |
|---|---|---|
| JP | 3720487 B2 | 11/2005 |
| JP | 2006-223871 A | 8/2006 |
| JP | 2009-131595 A | 6/2009 |
| KR | 20-0370275 Y1 | 12/2004 |
| KR | 10-0797144 B1 | 1/2008 |
| KR | 10-1027081 B1 | 4/2011 |
| KR | 10-1640481 B1 | 7/2016 |
| WO | 97/41904 A1 | 11/1997 |

* cited by examiner

[FIG. 1]
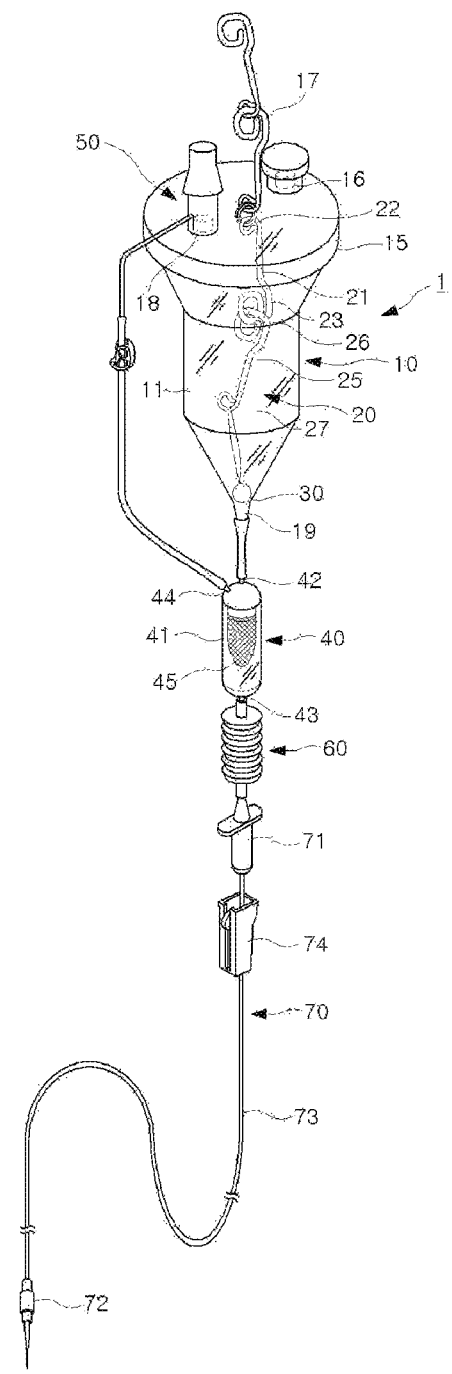

[FIG. 2]
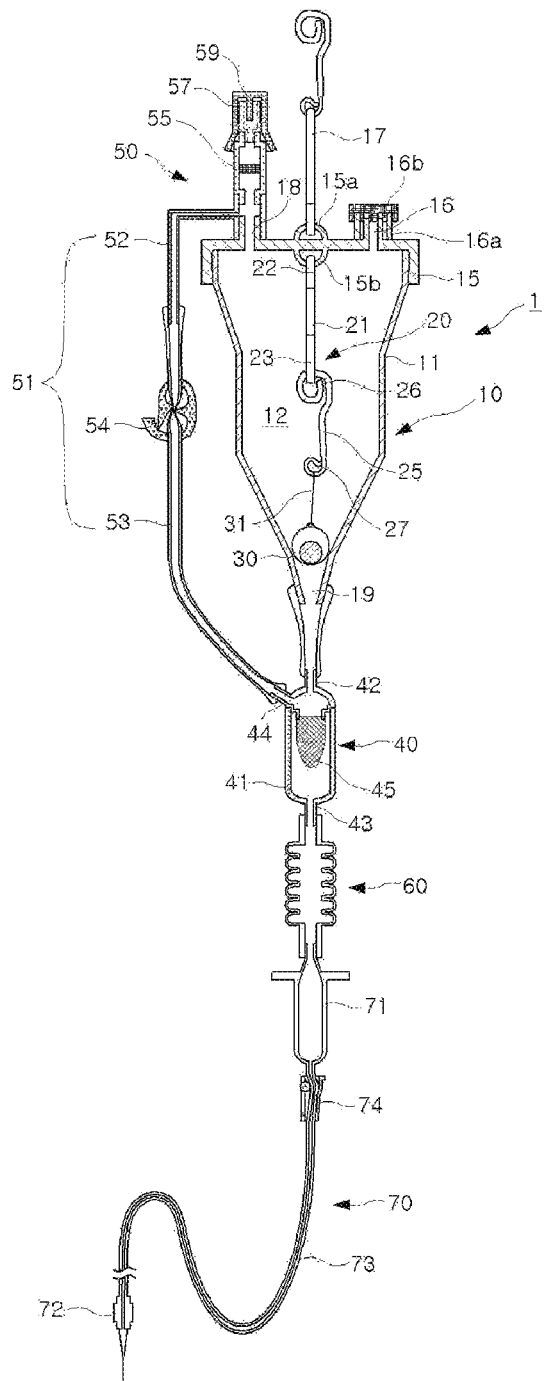

[FIG. 3]
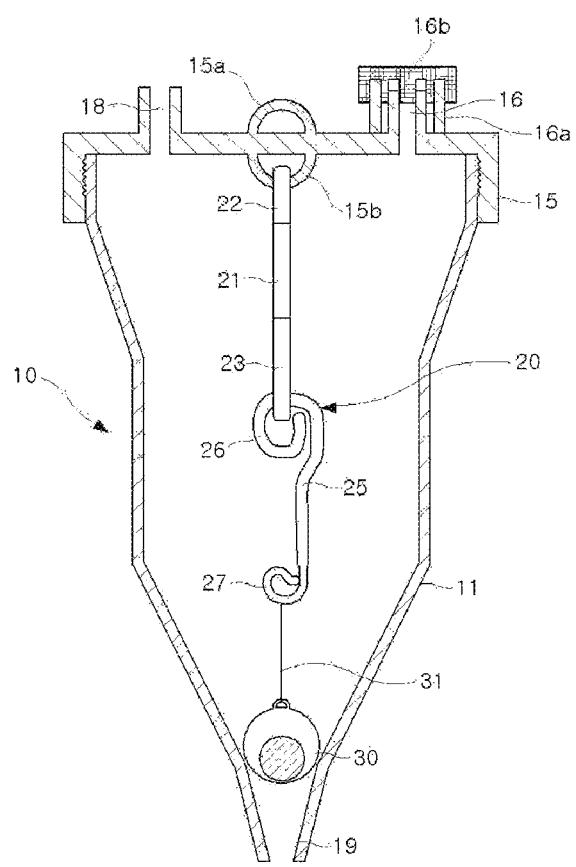

[FIG. 4]
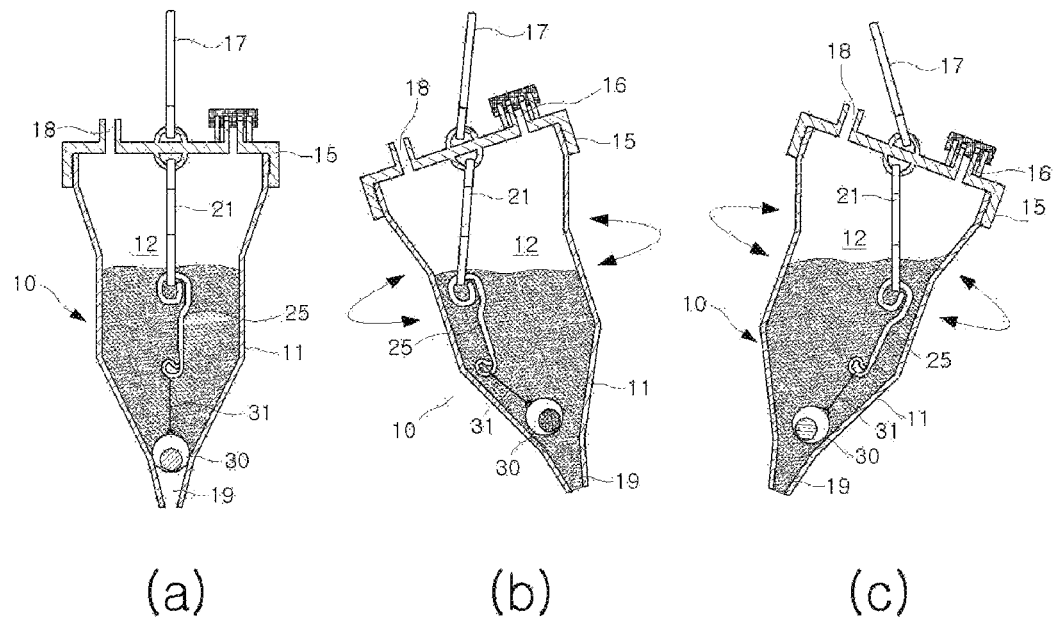
(a)　　　　　　(b)　　　　　　(c)
[FIG. 5]
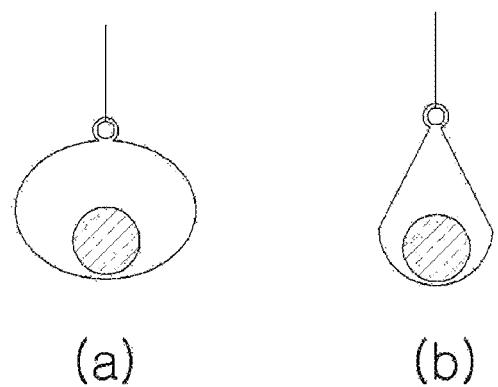
(a)　　　　　　(b)

[FIG. 6]
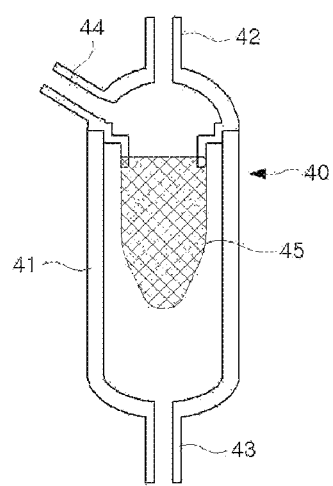

[FIG. 7]
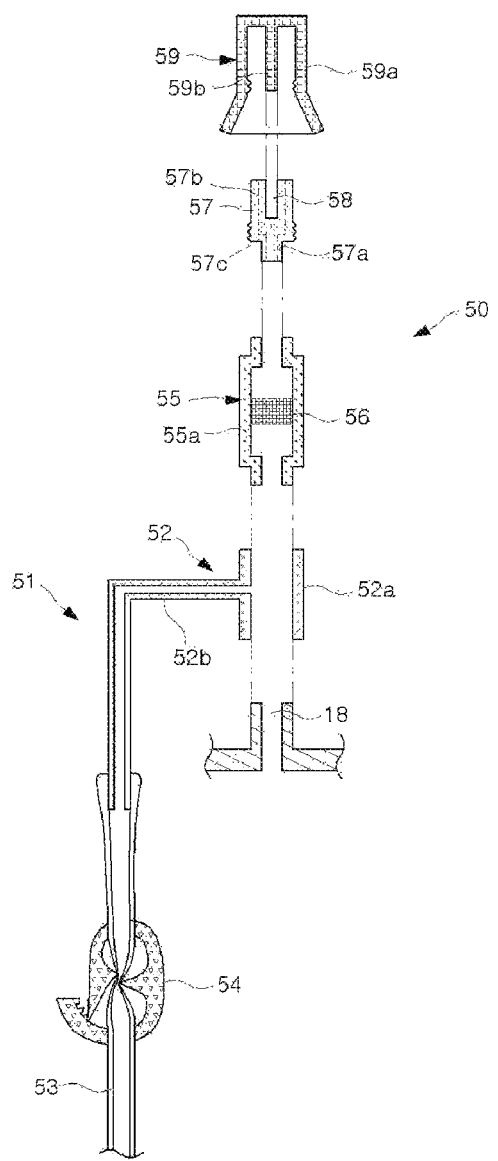

[FIG. 8]
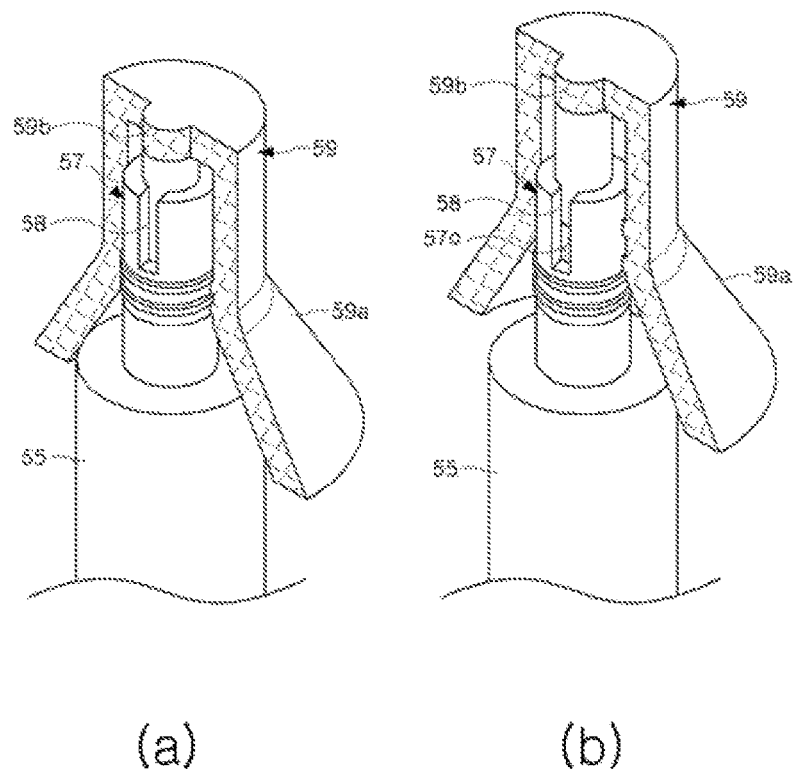
(a)　　　　　　(b)

[FIG. 9]
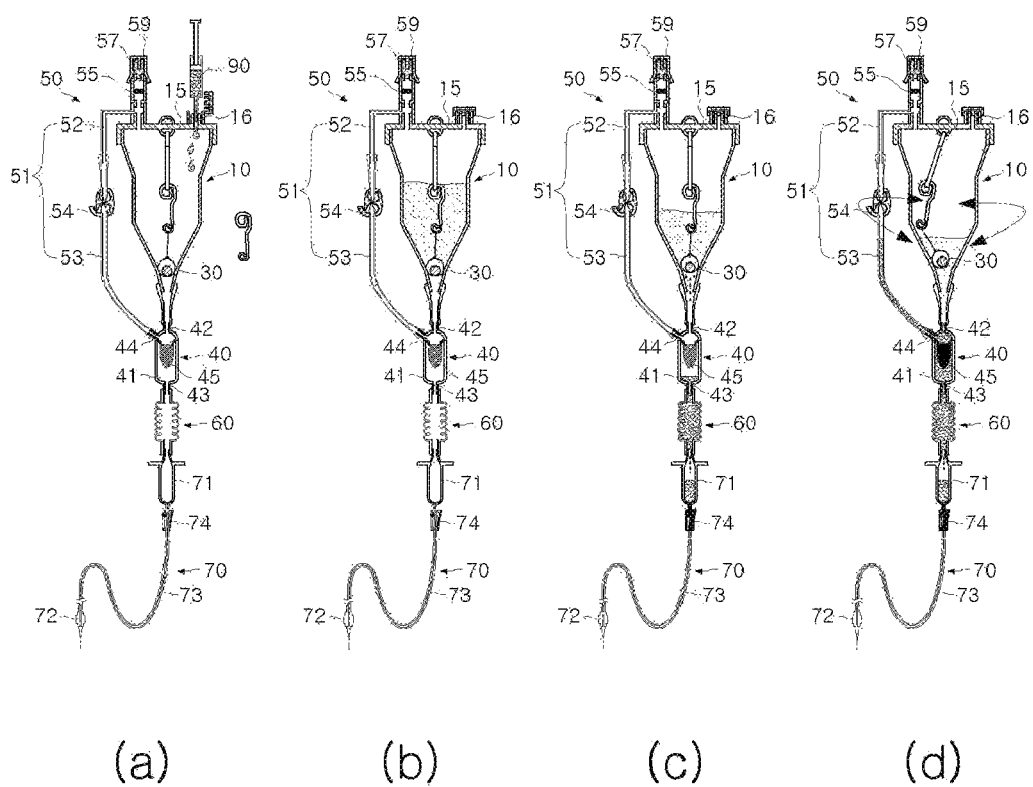
(a) (b) (c) (d)

[FIG. 10]
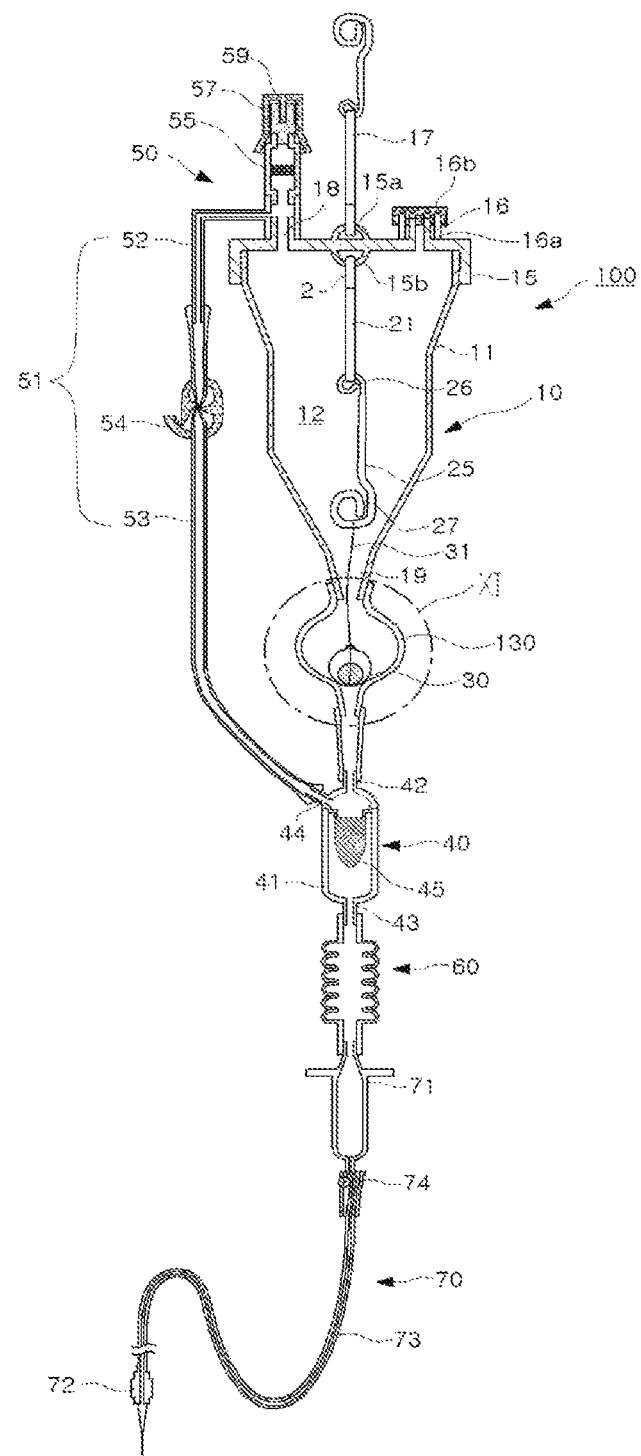

[FIG. 11]
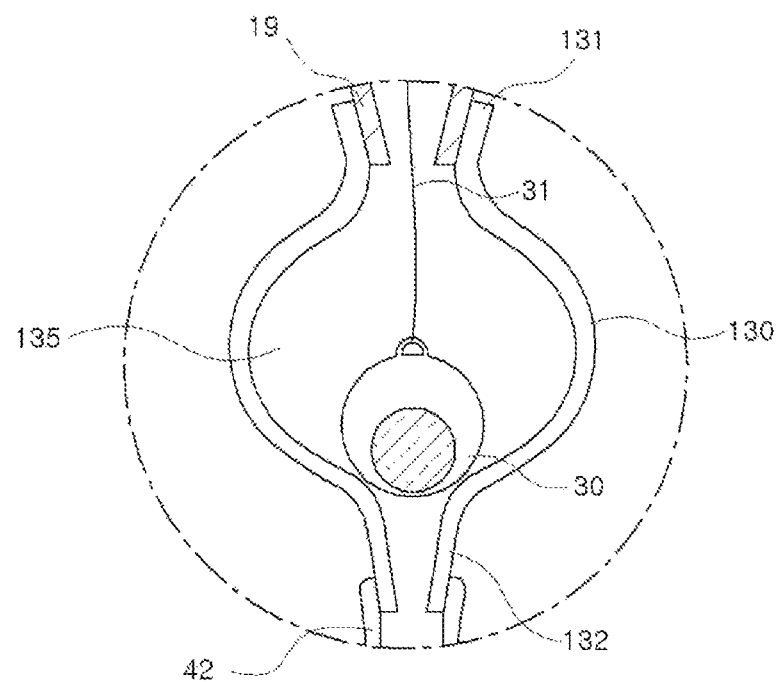

[FIG. 12]
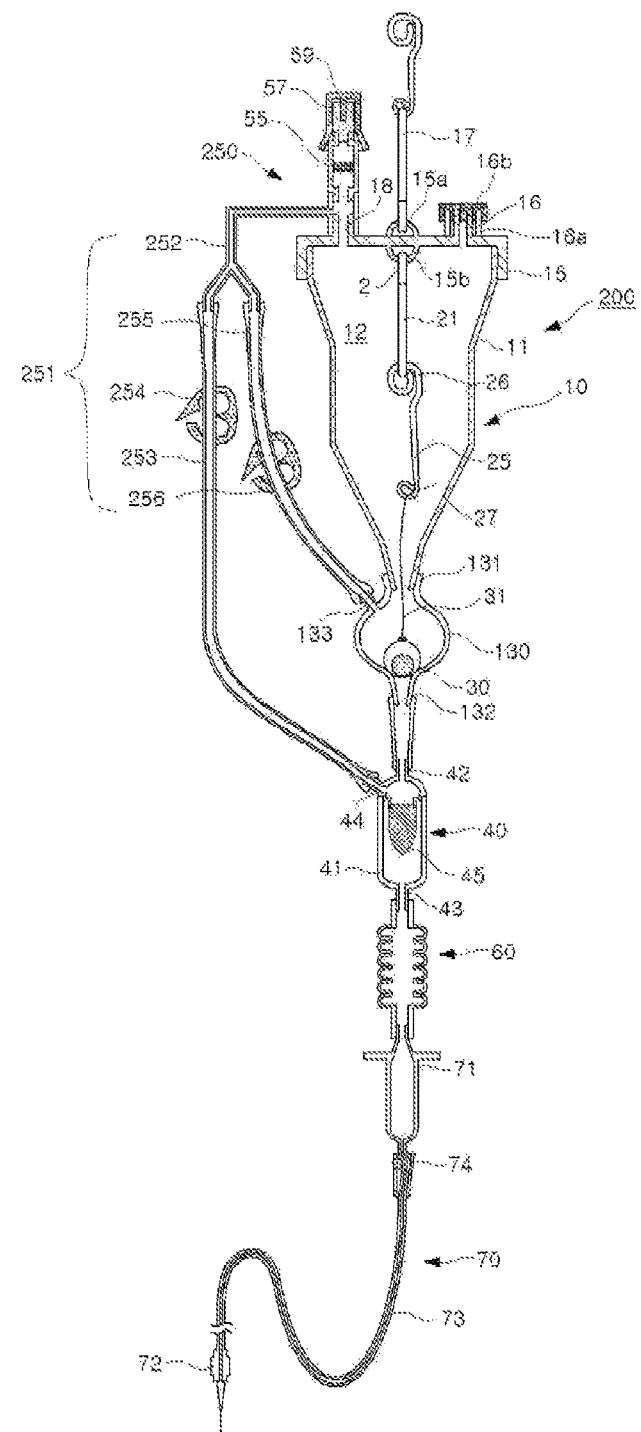

[FIG. 13]
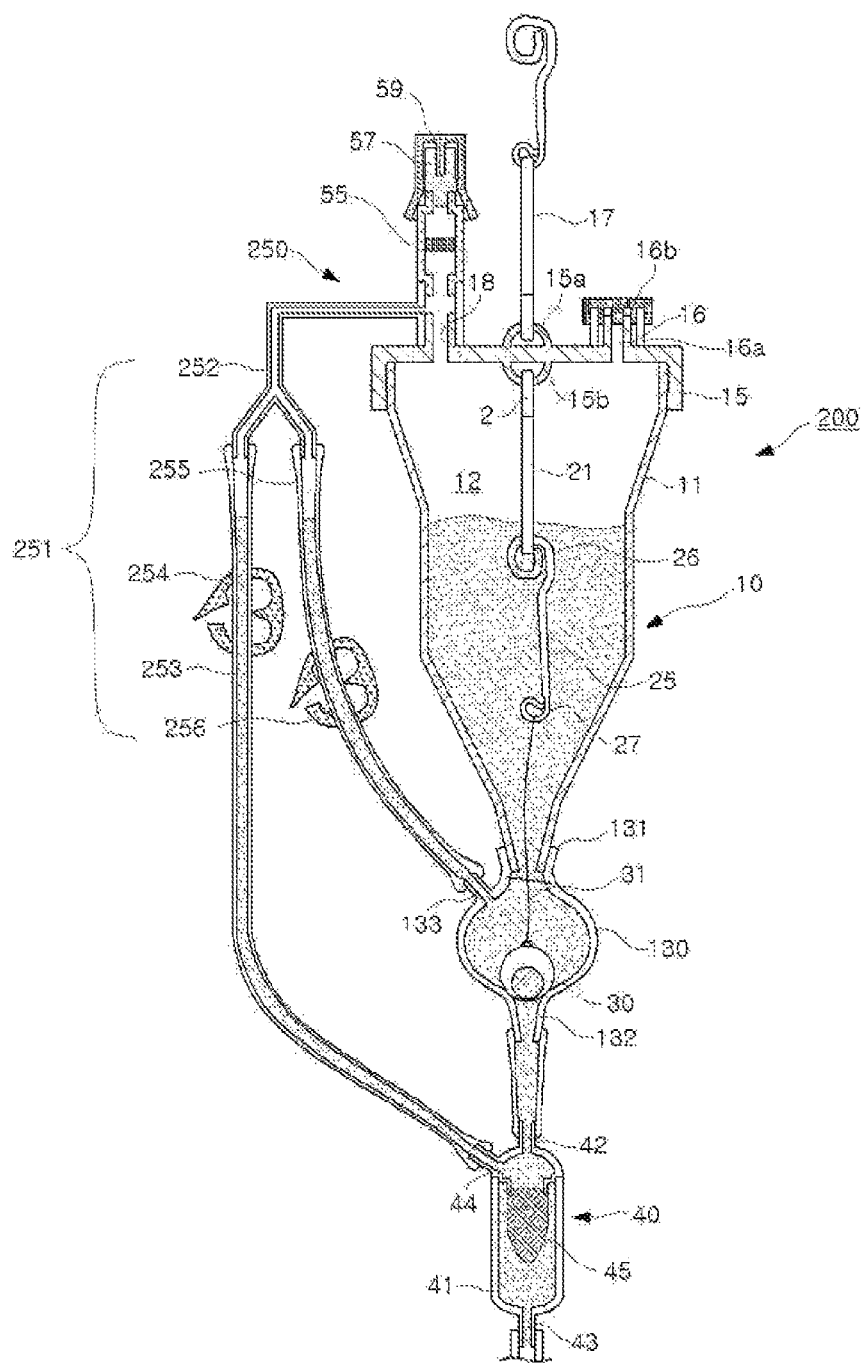

[FIG. 14]
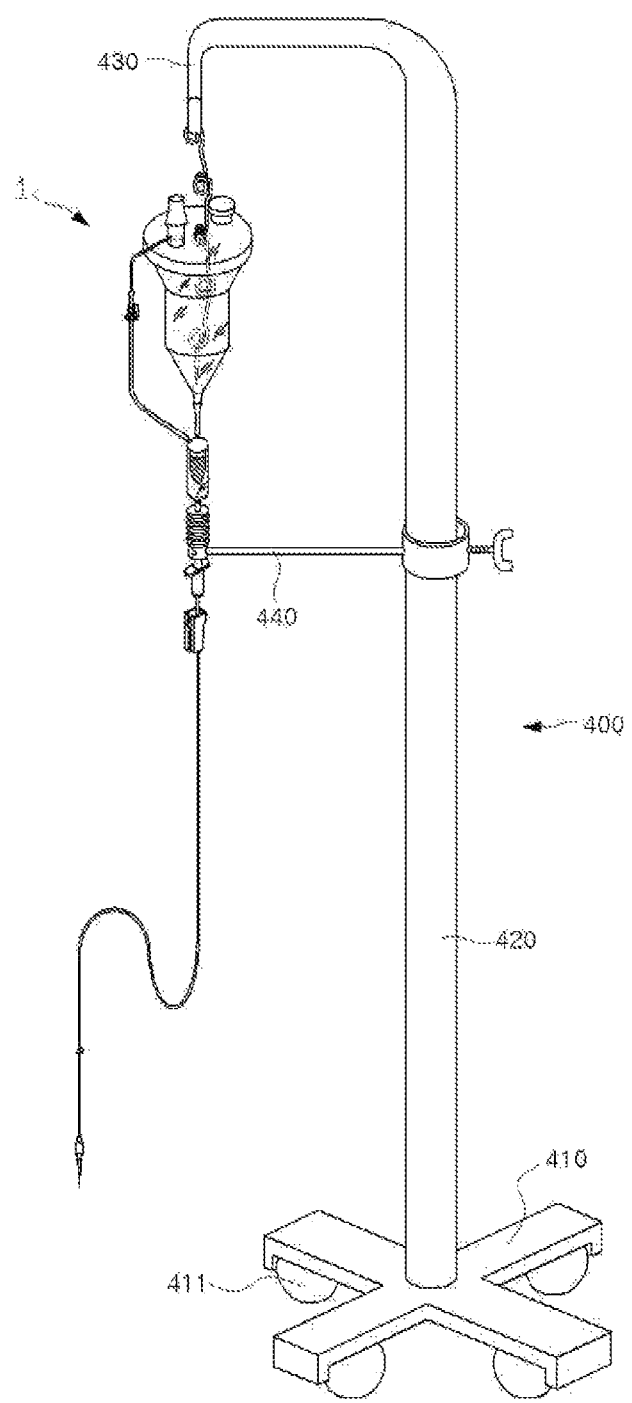

[FIG. 15]
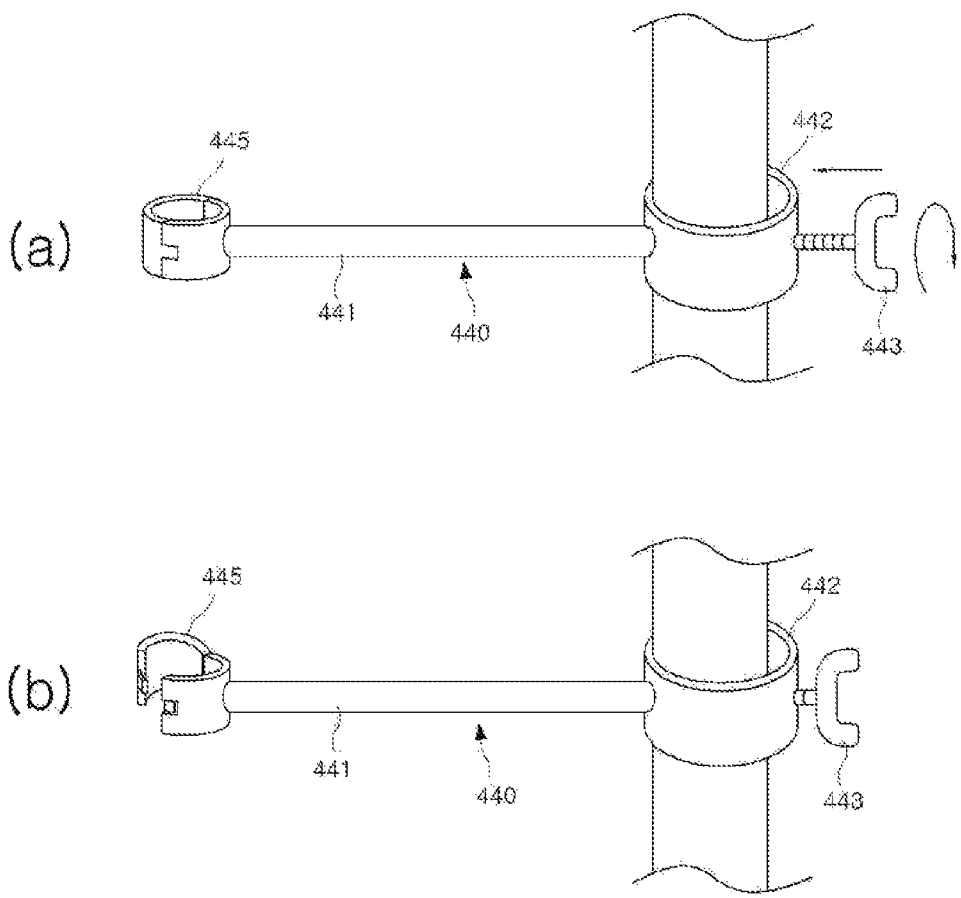

[FIG. 16]
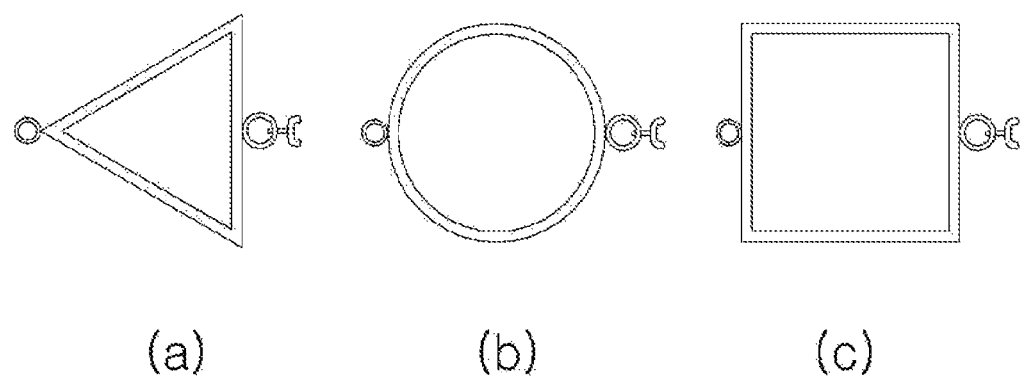
(a) (b) (c)

[FIG. 17]

MEDICAL INJECTION DEVICE

BACKGROUND OF THE INVENTION

Technical Field

The present invention relates to a medical injection device, and more particularly, to a medical injection device for preventing a target substance contained in an injection solution from being lost when the target substance is not settled or floated, and for evenly agitating the injection solution to be safely injected.

Background Art

As is well known, an injection solution device is used to inject liquid at a constant rate into muscles or blood vessels of a human or animal. Herein, the injection liquid means a mixture of saline (or Ringer's solution, nutrient solution, etc. that can be injected into the human), or a mixture in which a target substance such as a specific chemical solution or stem cell is mixed with saline (Ringer's solution, nutrient solution, etc.).

Herein, the chemical solution may be in any one form of a liquid chemical solution, a liquid chemical solution mixed with two or more chemicals, or a chemical solution in a form of an emulsion or a slurry.

In addition, the stem cell refers to cells capable of self-replicating and differentiating, and may be largely classified into embryonic stem cells and adult stem cells. Among them, it has been found that the adult stem cells are present in adipose tissues and bone marrow tissues of a human body in a large amount.

Currently, cells that can be easily used in a hospital include: stromal vascular fraction cells (SVF Cells) that can be obtained by taking adipose tissues, then enzymatically treating the same; adipose derived stem cells (ADSCs) that can be obtained by purifying the SVF Cells once again; and bone marrow derived mesenchymal stem cells (BMMSCs) that can be obtained by extracting a bone marrow fluid from bone marrow, followed by performing a cultivation process.

Recently, with the development of stem cell-based therapies, interest in stem cells has been increasing. As a result, equipment for facilitating the extraction of stem cells has been actively developed.

However, stem cells have characteristics in which they are easily settled (precipitated) under water due to a difference in specific gravity with water during an extraction process or after completing the extraction, have a tendency to adhere to plastic, and clot with each other to become easily solidified.

Due to such characteristics of the stem cells, if careful attention is not paid when injecting the extracted stem cells into the human body, significant cell loss may occur during the injection process, and as a result, therapeutic effects may be reduced.

In addition, when administering the stem cells in a lumped state or at a high concentration, blood vessels may be blocked by the stem cells to cause thrombosis, and an allergic reaction may be induced.

Further, when administering emulsion or slurry type substances (cells or substances in a form of not being dissolved in a solution), an additional process such as filtration is required for safety. Among the additional processes, even with minimal carelessness, the target substance to be injected may be easily damaged and effects thereof may be deteriorated.

Despite there being such risks, the development of an injection device for injecting the stem cells is very limited. When administering an injection solution using a conventional injection device, there is a problem that it may cause a fatal medical accident because there is no device that can control flowing of the injection solution at a desired injection rate or agitate the stem cells to be administered in a safe concentration.

PRIOR ART DOCUMENT

Patent Document

Korean Utility Model Registration No. 20-0370275 (published on Dec. 13, 2004)

SUMMARY OF INVENTION

Problems to be Solved by Invention

In consideration of the above-described circumstances, it is an object of the present invention to provide a medical injection device which: applies a vibration to the injection device to agitate an injection solution, such that a target substance contained in the injection solution may be injected with being maintained in an appropriate concentration; prevents the vibration that has been applied to the injection device from being transmitted to an injection needle, so as to prevent a person who receives the injection solution from being damaged; and freely control a level and an injection rate of the injection solution within a desired range, such that the injection solution may be more safely injected.

Means for Solving Problems

In order to accomplish the above object, there is provided a medical injection device including: a container including an internal storage space formed therein to contain and store an injection solution, and an injection solution outlet port formed at a lower portion thereof; an injection solution filter connected to the injection solution outlet port of the container to filter out the injection solution flown through the injection solution outlet port; a guide tube connected to a lower portion of the injection solution filter to provide a flow passage for injecting the injection solution filtered through and discharged out of the injection solution filter; and an injection solution level controller which is configured to control an opening degree for allowing an air to be flown into or discharged from the container, and connects a first level control port formed at an upper portion of the container and a second level control port formed at an upper portion of the injection solution filter to be communicated with each other.

Herein, the second level control port is preferably located at the uppermost portion of the injection solution filter.

In addition, the injection solution level controller may include: a branched connection tube formed by branching so as to connect the first level control port with the second level control port; a slit adapter which is connected to the branched connection tube and has a slit-shaped air inlet/outlet hole formed therein; and an air adjustment cap coupled to the slit adapter to control an opening degree of the air inlet/outlet hole.

Further, the branched connection tube may include: a branched tube having a first branched tube part formed therein so as to extend between a connection tube part which connects the first level control port with the slit adapter and the second level control port; and a first connection tube which connects the first branched tube part of the branched tube with the second level control port of the injection solution filter.

Further, the first connection tube may be made of a flexible material, and may include: a first connection tube clamp provided on an outer circumference thereof to press the first connection tube so as to control a size of a cross-sectional area of an internal flow passage defined therein.

In addition, the medical injection device may further include an air filter located between the slit adapter and the branched connection tube, wherein the air filter may include: a filter housing having an internal filtration space formed therein; and an air filter medium installed in the filter housing to filter air flowing through the air inlet/outlet hole.

Herein, the slit adapter may be formed integrally with the air filter.

In addition, the guide tube may further a liquid drop tube, an injection flow rate controller, and an extension tube, wherein the injection solution filter is preferably fully filled with the injection solution, while the liquid drop tube is preferably partially filled with the injection solution, so as to perform filtration and injection.

In addition, the medical injection device may further include an agitation means which is provided in the container, and when vibration occurs in the container, swings to agitate the injection solution in the container.

Further, the agitation means may include: a first agitator suspended and fixed to an upper side of the container so as to freely move within a limited range; and a second agitator connected to a lower end of the first agitator so as to freely move within a limited range, wherein the first agitator is preferably formed in such a way that a lower portion is heavier than an upper portion thereof, and the second agitator is preferably formed in such a way that an upper portion is heavier than a lower portion thereof.

Further, the first agitator and the second agitator may have upper and lower connecting rings which are formed by bending upper and lower end portions of a rod in a spiral shape, respectively, the upper connecting ring of the second agitator may be hooked to the lower connecting ring of the first agitator, the first agitator is preferably formed in such a way that the lower connecting ring is larger than the upper connecting ring, and the second agitator is preferably formed in such a way that the upper connecting ring is larger than the lower connecting ring.

Further, the container may be formed so as to have a cross-sectional reduced portion whose lower portion is reduced toward the injection solution outlet port, and the container may further include a vibration sensing ball housed in the lower cross-section reduced portion to open and close the injection solution outlet port according to the vibration applied to the container.

Further, the vibration sensing ball is more preferably connected to a lower end portion of the agitation means through a connecting line so as to move in conjunction therewith.

Further, the vibration sensing ball may have a lower portion with a weight larger than that of an upper portion thereof, and at least the lower portion preferably is formed as a curved portion so as to close the injection solution outlet port.

In addition, the medical injection device may further include: an expansion tube which connects the container with the injection solution filter, and has an enlarged cross-sectional area of an internal flow passage at a center portion in a longitudinal direction thereof; and a vibration sensing ball housed in the expansion tube to open and close a lower injection solution flow passage connected to the injection solution filter according to a vibration applied to the container.

Further, the expansion tube may further include a third level control port formed at an upper portion thereof, to which the injection solution level controller is connected.

Further, the injection solution level controller may include: a branched connection tube whose lower end portion is branched so as to connect the first level control port, the second level control port and the third level control port with each other; a slit adapter coupled to an upper open end portion of the branched connection tube; and an air adjustment cap fastened to an air inlet slit forming end of the slit adapter to adjust an opening degree of the air inlet slit.

Further, the branched connection tube may include: a branched tube having a second branched tube part formed so as to connect a connection tube part that connects the first level control port and the slit adapter with the second level control port and the third level control port; a first connection tube which connects the first branch end portion of the second branched tube part with the second level control port; and a second connection tube which connects the second branch end portion of the second branched tube part with the third level control port.

Further, the first connection tube and the second connection tube may be made of a flexible material, and respectively may include: a first connection tube clamp provided on an outer circumference of the first connection tube so as to control a cross-sectional area of an internal flow passage of the first connection tube; and a second connection tube clamp provided on an outer circumference of the second connection tube so as to control the cross-sectional area of the internal flow passage of the second connection tube.

Herein, the vibration sensing ball may be connected to a lower portion of the agitation means inside the container through a connecting line so as to move in conjunction therewith, and the vibration sensing ball may have a lower portion with a weight larger than that of an upper portion thereof, and the lower portion is preferably formed as a curved portion so as to close the lower injection solution flow passage.

In addition, the medical injection device preferably further includes a bellows connector which connects the injection solution filter with the guide tube, and is made of an elastic material.

In addition, the medical injection device may further include a hanger configured to movably hang and fix the container, and the hanger may further include a middle fixing bar configured to grasp and fix a lower portion of the bellows connector.

Furthermore, the middle fixing bar may be formed in a shape of a straight line, a circle, an ellipse or a polygon shape.

Advantageous Effects

The medical injection device according to the present invention may provide the following effects. The container containing the injection solution and the agitation means provided in the container are vibrated to agitate the injection solution, so as to allow the target substance contained in the injection solution to be injected at a uniform concentration with being sufficiently agitated, and thereby a fatal medical accident that may be caused by an nonuniform concentration of the target substance may be prevented.

In addition, if the injection solution is not agitated by applying vibration, the vibration sensing ball provided in the container or expansion tube may be automatically shut off a flow passage so as to block the injection solution from flowing downstream to be injected, and thereby the injection solution may be more safely injected.

Further, the vibration sensing ball is connected so as to move in conjunction with the vibration means through the connecting line, such that the injection solution outlet port may be smoothly opened and closed through the vibration sensing ball.

Further, the container and the filter and/or the expansion tube are connected with each other through the injection solution level controller, such that the level and the injection rate of the injection solution filled therein may be more freely controlled. In particular, in order to allow the injection solution to be subjected to a sediment filtration process inside the filter, the injection solution is injected while being filled in the filter at a preset level or more, thereby the target substance such as the stem cells may be stably filtered and injected without damage due to the injection solution filter medium, etc. More preferably, by performing the filtration and injection with the injection solution filter being fully filled and the liquid drop tube of the guide tube being partially filled, the injection solution may be efficiently filtered and injected.

Further, it is possible to prevent the vibration applied to agitate the injection solution by using the bellows connector from being transmitted to the injection needle, thereby preventing a person who receives the injection solution through an inserted injection needle from feeling inconvenience or a medical accident occurring.

Furthermore, the middle fixing bar is installed at the center portion of the hanger on which the injection device is mounted so as to hold and fix the lower portion of the bellows connector. Thereby, it is possible to enhance an agitation effect of the injection solution by applying sufficient vibration to an upstream side of the bellows connector including the container, and safely inject the injection solution by preventing the vibration from being transmitted to a downstream side of the bellows connector.

BRIEF DESCRIPTION OF DRAWINGS

FIG. 1 is a partial cutaway perspective view illustrating a medical injection device according to a first embodiment of the present invention.

FIG. 2 is a front cross-sectional view illustrating the medical injection device of FIG. 1.

FIG. 3 is an enlarged front cross-sectional view illustrating a container of FIG. 2.

FIGS. 4(*a*) to 4(*c*) are front cross-sectional views illustrating a process of vibrating the container of FIG. 3 to agitate the injection solution.

FIGS. 5(*a*) and 5(*b*) are front cross-sectional views illustrating respective modifications for a vibration sensing ball of FIG. 3.

FIG. 6 is an enlarged side cross-sectional view illustrating an injection solution filter of FIG. 2.

FIG. 7 is a front cross-sectional view illustrating an injection solution level controller illustrated in FIG. 2.

FIGS. 8(*a*) and 8(*b*) are partial cutaway perspective views illustrating opening and closing states of an air inlet/outlet hole according to a fastening state of an air adjustment cap.

FIGS. 9(*a*) to 9 (*d*) are front cross-sectional views illustrating an injection solution level control process inside the container and injection solution filter through the injection solution level controller of FIG. 2.

FIG. 10 is a perspective view illustrating a medical injection device according to a second embodiment of the present invention.

FIG. 11 is an enlarged front cross-sectional view illustrating an expansion tube of FIG. 8.

FIG. 12 is a perspective view illustrating a medical injection device according to a third embodiment of the present invention.

FIG. 13 is a front cross-sectional view illustrating the injection solution level controller of FIG. 10.

FIG. 14 is a front cross-sectional view illustrating a medical injection device according to a fourth embodiment of the present invention.

FIG. 15 is a plan view illustrating a middle fixing bar of FIG. 14.

FIGS. 16(*a*) to 16(*c*) are plan views illustrating respective modifications for the middle fixing bar of FIG. 15.

DETAILED DESCRIPTION OF THE INVENTION

[Mode for Carrying out Invention]

Figure 17A:
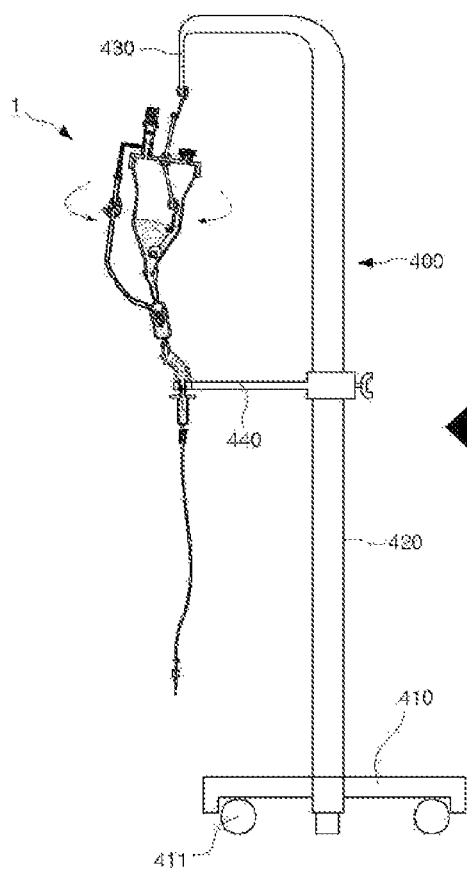
FIGS. 17(*a*) and 17(*b*) are front cross-sectional views illustrating states of vibrating the injection device to agitate an injection solution with the medical injection device being mounted using a hanger.

Hereinafter, preferred embodiments of the present invention will be described in detail with reference to the accompanying drawings, so that persons having common knowledge in the technical field to which the present invention pertains may easily implement the invention. However, the present invention may be realized in various forms, and it is not limited to the embodiments described herein. In the drawings, publicly known functions and configurations that are judged to be able to make the purport of the present invention unnecessarily obscure will not be illustrated. Referring to the drawings, wherein like reference characters designate like or corresponding parts throughout the several views.

FIG. 1 is a partial cutaway perspective view illustrating a medical injection device according to a first embodiment of the present invention.

Referring to FIG. 1, a medical injection device 1 according to the first embodiment of the present invention includes a container 10 having an agitation means 20 and a vibration sensing ball 30, an injection solution filter 40, an injection solution level controller 50, a bellows connector 60, and a guide tube 70. Thus, by continuously and regularly or irregularly applying vibration to the injection device, a target substance contained in an injection solution may be injected at a uniform concentration with the target substance being sufficiently agitated.

FIG. 2 is a front cross-sectional view illustrating the medical injection device of FIG. 1, and FIG. 3 is an enlarged front cross-sectional view illustrating the container of FIG. 2.

Referring to FIGS. 2 and 3, the container 10 includes an internal storage space 12 formed therein to contain and store the injection solution to be injected, an injection solution inlet port 16 formed at an upper portion thereof, through which the injection solution is introduced into the internal storage space 12, and an injection solution outlet port 19 formed at a lower portion thereof to supply the injection solution to a person who receives the injection solution through the injection solution filter 40, the bellows connector 60, and the guide tube 70.

In the present embodiment, as an example, the container 10 is made of glass or plastic, and is formed in a form of a transparent or translucent vessel in which a volume of the internal storage space 12 can be constantly maintained. In particular, the container includes a container body 11 for defining the internal storage space 12, and a container cover 15 screwed with the container body 11 so as to seal an upper opening portion thereof.

However, the present invention is not limited thereto, and of course, the container 10 may be configured in more various forms including a pouch so long as it can apply vibration while containing the injection solution therein to sufficiently vibrate the same so that target substance (stem cells, etc.) may be injected while having a uniform concentration.

As described above, in the present embodiment, the container 10 is formed by dividing into the container body 11 and the container cover 15, thereby opening and closing the upper opening portion of internal storage space in the container body 11 through the container cover 15. Accordingly, it is possible to increase convenience in manufacturing the container 10 in a vessel form and using the same.

Meanwhile, the container cover 15 may be provided with at least one injection solution inlet port 16 through which the injection solution is introduced into the internal storage space 12, and a first level control port 18 for controlling a level of the injection solution.

In addition, the injection solution inlet port 16 may further include a hollow protection wall 16a for surrounding and protecting the injection solution inlet port 16, and an inlet port cap 16b fitted on the protection wall 16a to close the injection solution inlet port 16.

An upper end of the injection solution level controller 50 is connected to the first level control port 18 while a lower end thereof extends downward. The injection solution level controller 50 controls a degree in which an inside of the container 10 is opened to an outside, that is, to the atmosphere, together with the injection solution filter 40 to be described below. Therefore, a flow rate (injection rate) of the injection solution flowing from the internal storage space 12 to the downstream side may be controlled.

Meanwhile, the container cover 15 has upper and lower fixing rings 15a and 15b formed on upper and lower surfaces thereof, respectively, at a center portion between the injection solution inlet port 16 and the first level control port 18.

Herein, the upper fixing ring 15a is used for hanging a latch 17 extending upward and configured to movably suspend and attach the container 10 to a hanger 400 (see FIGS. 14 and 17), and the lower fixing ring 15b is used for hanging the agitation means 20 extending downward and configured to agitate the injection solution inside the container 10.

Each of the latches 17 may be hooked and connected at a required length, similar to a first agitator 21 and a second agitator 25 of the agitation means 20 to be described below. To this end, the latch is configured in such a way that upper and lower end portions of a rod may be bent in a spiral shape so that upper and lower connecting rings are formed therein.

As such, the container 10 is suspended and attached so as to freely move within a limited range through the latches 17, such that the container 10 may swing so as to perform a pendulum motion or axial precession by an external force (a force generated by a user manually shaking the container or by a vibrating device provided in the hanger), and thereby agitating the injection solution.

In addition, the container body 11 is formed in a substantially hollow conical shape, and has the injection solution outlet port 19 formed at the lowermost end portion thereof, that is, an apex of the cone, through which the injection solution selectively passes.

As such, since the lower portion of the container 10 is formed so as to have a cross-section reduced portion whose lower portion is reduced in a hollow conical shape, the target substance such as stem cells having sedimentation properties of the injection solution contained in the container 10 may flow along an inner inclined surface thereof, thus to be completely discharged through the injection solution outlet port 19 without remaining in the container.

The agitation means 20 is suspended from the lower fixing ring in the container 10 so as to freely move within a limited range in conjunction with the vibration applied to the container 10 to agitate the injection solution contained therein.

In the present embodiment, the agitation means 20 includes, as an example, the first agitator 21 whose upper end is suspended from the lower fixing ring 15b of the container cover 15 and lower end extends downward, and the second agitator 25 whose upper end is hooked to the lower end of the first agitator 21 and lower end extends downward.

The first agitator 21 and the second agitator 25 have upper and lower connecting rings 22, 23, 26 and 27 which are formed by bending upper and lower end portions of a rod in a spiral shape, respectively.

The upper connecting ring 22 of the first agitator 21 is suspended from the lower fixing ring 15b of the container cover 15 so as to freely move within a limited range, and the upper connecting ring 26 of the second agitator 25 is hooked to the lower connecting ring 23 of the first agitator 21 so as to freely move within a limited range.

Hereinafter, a process of agitating the injection solution using the first agitator 21 and the second agitator 25 will be described in more detail with reference to FIG. 4.

FIGS. 4(a) to 4(c) are front cross-sectional views illustrating a process of vibrating the container of FIG. 3 to agitate the injection solution.

As illustrated in FIG. 4, when an external force (a force generated by a user manually shaking the container or by a vibrating device provided in the hanger) is applied to the container 10, the container 102 swings and performs a pendulum motion or axial precession.

Further, the pendulum motion or the axial precession of the container 10 is transmitted to the first agitator 21 and the second agitator 25 which are integrally connected with each other in the container 10 through the rings, such that the first agitator 21 and the second agitator 25 swing and stir to agitate the injection solution.

At this time, in order to enhance the agitation effect of the injection solution through the first agitator 21 and the second agitator 25, preferably, the first agitator 21 is formed in such a way that the lower connecting ring 23 is larger than the upper connecting ring 22, and the second agitator 25 is formed in such a way that the upper connecting ring 26 is larger than the lower connecting ring 27.

As such, the first agitator 21 is formed in such a way that the lower connecting ring 23 is larger than the upper connecting ring 22, and the second agitator 25 is formed in such a way that the upper connecting ring 26 is larger than the lower connecting ring 27, thereby the first agitator 21 is formed in such a way that a lower portion is heavier than an upper portion thereof, and the second agitator 25 is formed in such a way that an upper portion is heavier than a lower portion thereof.

Therefore, the first agitator 21 has a center of gravity at the lower portion thus to be stable, while the second agitator 25 has a center of gravity at the upper portion thus to be unstable. Accordingly, when a vibration occurs in the container 10, the first agitator 21, whose center of gravity is stable, has no change in a height, thus to swing mainly in a horizontal direction while performing the pendulum motion and the axial precession.

On the other hand, the second agitator 25, whose center of gravity is unstable, swings in the horizontal direction, and at the same time, vertically swings to perform an irregular pendulum motion and axial precession.

That is, the irregular pendulum motion and axial precession do not clearly occur in the upper portion of the second agitator 25, which is hooked to the lower connecting ring of the first agitator 21 and has a relatively large weight, but clearly occurs toward the lower portion whose center of gravity is unstable. Thus, the lower connecting ring 27 of the second agitator 25 performs the most irregular pendulum motion and axial precession.

Meanwhile, the stem cells of the target substance have a strong tendency to be settled in the container 10, and may be adsorbed and solidified on the inner wall adjacent to the injection solution outlet port 19 of the container 10. Therefore, the concentration of stem cells is increased toward the lower portion of the container 10, and particularly, a coagulation phenomenon often occurs on the inner wall adjacent to the injection solution outlet port 19.

In the agitation means 20 of the present embodiment, the lower connecting ring 23 of the first agitator 21 and the upper connecting ring 26 of the second agitator 25 stably performs the pendulum motion and the axial precession mainly in the horizontal direction. Therefore, a directional convection phenomenon may be generated in a middle portion of the container 10, and an agitation occurs across the entire injection solution due to the above-described convection phenomenon.

On the other hand, the lower connecting ring 27 of the second agitator 25 irregularly performs the pendulum motion and the axial precession in the horizontal and vertical directions. Therefore, a directional convection phenomenon does not occur.

In other words, an agitation that affects across the entire injection solution does not occur in the lower portion of the container 10, but the injection solution in the lower portion of the container 10 is intensively stirred, and only in a local portion, the lower portion of the container may exhibit superior agitating performance to the lower portion of the first agitator 21 and the upper portion of the second agitator 25.

Therefore, the above-described agitation means 20 is very suitable for an injection device 100 provided with the container 10 in which the concentration of stem cells is increased toward the lower portion of the container 10, such that a large amount of solidification phenomenon occurs on the inner inclined wall adjacent to the injection solution outlet port 19, and in which the cross-section reduced portion is formed toward the injection solution outlet port 19.

As such, by agitating the injection solution through the above-described agitation means 20, it is possible to prevent the solidification of the substances (stem cells, etc.) contained in the injection solution, and uniformly maintain the concentration of the target substance in the injection solution. Therefore, it is possible to prevent a risk that the stem cells are precipitated and administered at a high concentration or injected in a lumped state.

The vibration sensing ball 30 is housed in the lower cross-section reduced portion of the container 10 to open and close the injection solution outlet port 19 of the container 10 according to the vibration applied to the container 10.

In other words, since the vibration sensing ball 30 has a diameter larger than a diameter of the cross-section of the injection solution outlet port 19, normally, the ball is brought into close contact with the inclined surface of the lower cross-section reduced portion of the container 10 to close a flow passage defined therein. As a result, the injection solution is prevented from flowing out of the container 10 through the injection solution outlet port 19.

However, when applying a vibration to the container 10 to swing the same, the container 10 performs the pendulum motion and the axial precession as described above, and the vibration sensing ball 30 swings together therewith to intermittently open the injection solution outlet port 19.

In the present embodiment, as an example, the vibration sensing ball 30 is formed as a spherical body having a substantially circular cross-sectional shape, in which an eccentric weight is contained in an inner lower portion thereof so that the lower portion is heavier than the upper portion.

That is, by forming the vibration sensing ball 30 as a spherical body, the injection solution outlet port 19 is adapted so as to perform an opening/closing operation always at the same position. In addition, even if attenuating the pendulum motion or the axial precession of the container 10 which is swinging, an isolated space formed by the vibration sensing ball 30 being spaced apart from the lower inclined surface of the container 10 is constantly decreased over time. Therefore, it is possible to prevent a sudden change in the flow rate of the injection solution.

In addition, the vibration sensing ball 30 is formed so as to have a center of gravity at the lower side, that is, have a lower portion with a weight larger than that of an upper portion thereof, such that the injection solution outlet port 19 may perform the opening/closing operation while being kept always in an upright shape similar to a dent which inhibits a rolling motion in the process of swinging to open the injection solution outlet port 19. For this, at least the lower portion of the vibration sensing ball is formed as a curved portion.

FIGS. 5(*a*) and 5(*b*) are front cross-sectional views illustrating respective modifications for the vibration sensing ball of FIG. 3.

In the present embodiment, a configuration, in which the vibration sensing ball 30 is formed as a spherical body having a circular cross-sectional shape, is described as an example, but the present invention is not limited thereto. Of course, as illustrated in FIG. 5, so long as the center of gravity is located at the lower side and at least the lower portion has a curved portion for uniformly opening and closing the injection solution outlet port forming the cross-section reduced portion, the vibration sensing ball may be formed as spherical bodies having more various sectional shapes including an ellipse or a fan shape.

In particular, as illustrated in FIG. 5(*b*), the vibration sensing ball 30 is formed as a spherical body having a fan cross-sectional shape in which upper and lower portions are asymmetric with respect to each other. Accordingly, the lower portion may be formed in a hemispherical shape to smoothly perform the opening/closing operation of the injection solution outlet port 19, and the upper portion may be formed in a conical shape to enhance the agitation effect of the injection solution in the lower cross-section reduced portion of the container 10.

Particularly, in the present embodiment, a configuration, in which the vibration sensing ball 30 is connected to the lower end portion of the above-described agitation means 20, that is, the lower connecting ring 27 of the second agitator 25 through a connecting line 31 so as to move in conjunction therewith, is described as an example.

As such, the vibration sensing ball 30 is connected to the lower connecting ring 27 of the second agitator 25 through the connecting line 31, such that the movement of the vibration sensing ball 30 is increased in response to the movement of the agitation means 20. Thereby, the injection solution outlet port 19 may more smoothly perform the opening/closing operation, as well as the agitating effect of the injection solution in the cross-section reduced portion of the container 10 may be enhanced.

Referring to FIGS. 1 and 2 again, the injection solution filter 40 is connected to the injection solution outlet port 19 of the container 10 to filter out the injection solution flown through the injection solution outlet port 19 by using the injection solution filter medium 45 to filter the lumps contained in the injection solution.

FIG. 6 is an enlarged side cross-sectional view illustrating the injection solution filter of FIG. 2.

Referring to FIG. 6, in the present embodiment, the injection solution filter 40 includes a filter housing 41 and an injection solution filter medium 45 installed in the filter housing 41.

Herein, the filter housing 41 provides a filtration space for filtering the injection solution introduced from the container 10 using the injection solution filter medium 45 installed therein, and a filter inlet port 42 connected to the injection solution outlet port 19 of the container is formed at an upper end thereof, with a filter outlet port 43 connected to the bellows connector 60 being formed at a lower end thereof.

Therefore, the injection solution introduced from the container 10 through the filter inlet port 42 flows in the filter housing 41 with being maintained at a level of a predetermined height or higher, and is moved to the guide tube 70 through the bellows connector 60 connected to the filter outlet port 43.

At this time, while the injection solution flows downward through the injection solution filter medium 45 installed in the filter housing 41, the lumped substances contained in the injection solution are substantially filtered while allowing the target substance such as stem cells to pass therethrough.

The injection solution filter medium 45 used in the present embodiment may include, as an example, a bag-filter having a dense membrane structure known in the art. However, so long as the lumped substances in the injection solution can be filtered while allowing the target substance such as stem cells to pass, filter media of various shapes and materials may be used.

Further, the filter housing 41 has a second level control port 44 formed at the upper portion thereof, to which the injection solution level controller 50 is connected to control an opening degree to an outside, so as to control the level and the injection rate of the injection solution to be filled in the filter housing 41 in associated with the container 10.

Herein, the second level control port 44 should maintain at least the injection solution level higher than an installation height of the injection solution filter medium 45 so as to induce the sediment filtration process of the injection solution through the injection solution filter medium 45. In consideration of efficiency, it is more preferable that the second level control port adjacent to the filter inlet port 42 is formed at the uppermost portion of the filter housing, so that the filtering process of the injection solution may be performed while the injection solution is fully filled in the filter housing 41.

That is, when injecting the target substance with the filter housing 41 being not filled, it is highly likely to damage the target substance such as cells because the injection solution is caught by the injection solution filter medium 45

Therefore, when performing the filtering process of the injection solution while the inside of the filter housing 41 is fully filled with the injection solution, the lumped substance contained in the target substance such as stem cells may be stably removed without being damaged by the injection solution filter medium, that is, the injection solution filter medium 45 of the bag filter form.

In particular, as described above, when performing the filtering process of the injection solution while the filter housing 41 is fully filled up to the uppermost stream thereof with the injection solution, even if the container 10 swings due to an external force, the injection solution may be stably injected without flowing of the injection solution inside the filter housing 41. This is based on a principle in which a lot of shaking is generated inside of the container partially filled with the material due to the external force, but shaking is not generated or is limitedly generated inside of the container fully filled with the material even when applying an external force.

Therefore, in order to more efficiently filter and inject the injection solution, it is preferable that the injection solution filter 40 is fully filled with the injection solution so that the injection solution does not always fluctuate due to the external shaking, and in order to observe and control the injection rate of the injection solution, a liquid drop tube 71 provided in the guide tube 70 is partially filled with the injection solution.

As described above, the injection solution level controller 50 is configured to control the opening degree for allowing the air to be flown into or discharged from the container, and connects the first level control port 18 formed at the upper portion of the container 10 with the second level control port 44 formed at the upper portion of the injection solution filter 40 to be communicated with each other. Therefore, it is possible to control the level of the injection solution filled in the container 10 and the injection solution filter 40 and the injection rate of the injection solution flowing through the guide tube 70.

A configuration, in which the bellows connector 60 connects the injection solution filter 40 with the guide tube 70, is made of an elastic material to be bent, and has a plurality of corrugations in a longitudinal direction, is described as an example.

That is, as described above, in order to agitate the injection solution, it is necessary for the container 10 to swing. Thereby, a kinetic energy generated due to the swing is transmitted to an injection needle 72 along the guide tube 70, such that a person who receives the injection solution through the inserted injection needle 72 may be discomforted, and minor abrasions to fatal medical accidents may occur.

Therefore, in the present embodiment, the injection solution filter 40 and the guide tube 70 are connected by using the bellows connector 60, such that the vibration transmitted to the container 10 so as to agitate the injection solution is blocked by a corrugated portion of the bellows connector 60, and thereby prevents it from being transmitted to the downstream side.

The guide tube 70 is connected to the lower portion of the bellows connector 60 to provide the flow passage for injecting the injection solution filtered through and discharged out of the injection solution filter 40.

In the present embodiment, as an example, the guide tube 70 includes the liquid drop tube 71, the injection needle 72, an extension tube 73, and an injection flow rate controller 74.

Herein, the liquid drop tube 71 is connected to the lower portion of the bellows connector 60, and allows a user to observe the injection solution that drops in a droplet state (water drop form) via the injection solution filter 40 from the container 10 at a desired injection rate while maintaining a constant level. Accordingly, the user may intuitively control the injection rate of the injection solution while observing the supplied injection solution through the liquid drop tube.

In addition, the injection flow rate controller 74 is provided on the extension tube 73 connecting the liquid drop tube 71 with the injection needle 72 to control the injection flow rate of the injection solution.

However, the present invention is not limited thereto. Of course, so long as it can be connected to the lower portion of the bellows connector 60 to inject the injection solution, the guide tubes 70 may be formed in various ways by adding or subtracting various components known in the art.

FIG. 7 is a front cross-sectional view illustrating the injection solution level controller illustrated in FIG. 2, and FIGS. 8(*a*) and 8(*b*) are partial cutaway perspective views illustrating opening and closing states of the air inlet/outlet hole according to a fastening state of the air adjustment cap.

Referring to FIGS. 7 and 8, as an example, the injection solution level controller 50 according to the present embodiment includes a branched connection tube 51, a slit adapter 57, and an air adjustment cap 59.

Herein, the branched connection tube 51 includes a branched tube 52 formed by branching so as to connect the first level control port 18 with the second level control port 44, and a first connection tube 53.

The branched tube 52 has a first branched tube part 52*b* formed therein so as to extend between a connection tube part 52*a* which connects the first level control port 18 with the slit adapter 57 and the second level control port 44.

The first connection tube 53 connects the first branched tube part 52*b* of the branched tube 52 with the second level control port 44 of the injection solution filter 40.

Herein, the first connection tube 53 is made of a flexible material, and includes a first connection tube clamp 54 provided on an outer circumference thereof to press the first connection tube 53 so as to control a size of a cross-sectional area of a fluid-communicated internal flow passage defined therein.

The slit adapter 57 is formed in a substantially hollow cylindrical shape so as to form an inner air inlet/outlet hole 57*c*, and includes a branched tube connection part 57*a* formed at a lower end portion thereof so as to be inserted and joined to an upper open end of the connection tube part 52*a* of the branched connection tube 51, and a cap fastening part 57*b* formed at an upper end portion thereof so as to have at least one open slit 58 cut along a side wall surface to which the air adjustment cap 59 is screwed.

The air adjustment cap 59 is screwed with the cap fastening part 57*b* of the slit adapter 57, such that the opening degree of the air inlet/outlet hole 57*c* may be controlled through the open slit 58 according to the degree of a fastening height controlled by tightening or loosening the screw.

Herein, the air adjustment cap 59 includes a cap body 59*a* formed in a trumpet shape so as to have an diameter increased toward a lower side from an upper closed end portion, a female screw formed on an inner circumference of the cap body to be screwed with the cap fastening part 57*b* of the slit adapter 57, and an opening/closing protrusion 59*b* which protrudes inward from the upper closed end and is inserted into the air inlet/outlet hole 57*c* to close the container.

Meanwhile, the injection solution level controller may further include an air filter 55 located between the slit adapter 57 and the branched connection tube 51 to filter the air introduced through the air inlet/outlet hole 57*c*. The slit adapter is formed integrally with the air filter.

The air filter 55 includes a hollow cylindrical filter housing 55*a* connecting the slit adapter 57 with the branched connection tube 51 and having a space formed therein to be communicated with the air inlet/outlet hole 57*c*, and an air filter medium 56 inserted in a space of the filter housing 55*a* for filtering the air introduced through the air inlet/outlet hole 57*c*.

Herein, the air filter medium 56 preferably includes an ultrafine filter or a high-efficiency particulate arresting (HEPA) filter so as to prevent external foreign contaminants from entering through the air inlet/outlet hole 57*c*.

The ultrafine filter has very small mesh holes of 0.1 to 0.2 micrometers or less, such that very small substances, bacteria, viruses, etc., floating in the air may be captured or inflowing thereof may be suppressed, and thereby minimizing the possibility of contamination due to the air.

Therefore, even if injecting the injection solution into the persons in the contaminated environment, the foreign matters, bacteria, virus, etc. may be removed by the air filter medium 56, such that it is possible to more safely inject the injection solution.

FIGS. 9(*a*) to 9(*d*) are front cross-sectional views illustrating an injection solution level control process inside the container and the injection solution filter through the injection solution level controller of FIG. 2.

First, as illustrated in FIGS. 9(*a*) and 9(*b*), in a state in which both the injection flow rate controller 74 of the guide tube 70 of the present embodiment and the first connection tube clamp 54 are closed, the injection solution containing the target substance is injected through the injection solution inlet port 19 of the container 10 using an injector 90 and a connection tube (not illustrated) to fill the inside of the container.

At this time, the injection solution outlet port 19 is closed by the vibration sensing ball 30, such that the injection solution filled in the container 10 cannot flow downstream, and remains with being filled in only the container 10.

Next, as illustrated in FIG. 9(*c*), when pressing the liquid drop tube 71 of the guide tube 70 by hand, an inner air pressure of the injection solution that has been filled from the lower portion of the container 10 closed by the vibration sensing ball 30 to the injection flow rate controller 74 is increased to push the vibration sensing ball 30 upward, and the injection solution flows down through the open injection solution outlet port 19 of the container 10.

Then, while repeating the process of pressurizing the liquid drop tube 71 of the guide tube 70, the flow rate of the injection solution flowing downward is controlled so that the injection solution is raised to a predetermined level in the liquid drop tube 71.

At this time, during the injection solution passing through the injection solution filter 40 then flowing down, the injection solution does not immediately flow down due to a diameter difference between the bellows connector 60 and the liquid drop tube 71, and remains in the bellows connector 60 with being filled up to the lower portion of the filter.

Thereafter, the injection solution filled between the bellows connector 60 and the lower portion of the injection solution filter 40 cannot be discharged with being trapped in the upper portion of the liquid drop tube 71, thereby maintaining a state in which it cannot no longer flow down due to the air having the increased pressure and remains therein.

Next, with the first connection tube clamp 54 being open, by performing the pendulum motion and the axial precession on the vibration sensing ball 30 together with the first agitator 21 and the second agitator 25 while shaking the container 10 by hand, the injection solution with being agitated continuously flows down through the open injection solution outlet 19. Then, the inner upper space of the injection solution filter 40, from which the air has escaped, is filled with the injection solution flowing down from the container 10, while the air filled above the injection solution filter 40 is discharged through the first connection tube 53.

When the injection solution continuously flows down from the container 10 into the injection solution filter 40 while continuously shaking, the injection solution fills the first connection tube 53 until the level reaches the same height as the container 10. This is possible because the first level control port 18 of the container 10 and the second level control port 44 of the injection solution filter 40 are simultaneously connected through the branched connection tube 51 of the injection solution level controller 50 to maintain the same open state as each other.

As illustrated in FIG. 9(*d*), when opening the injection flow rate controller 74 of the guide tube 70 with the injection solution flowing downward through the above-described processes being fully filled in the inner space of the injection solution filter 40, the injection solution, which has been filled due to maintaining a state in which the inner space of the injection solution filter 40 is fully filled with the injection solution as it is, and maintaining the same level in the container 10 and the first connection tube 53, flows down and is injected into the person who receives the injection solution via the liquid drop tube 71 of the guide tube 70, the extension tube 73 and the injection needle 72.

Of course, in order to allow the injection solution that has been filled in the container 10 to be continuously flown down, the container 10 should be continuously vibrated to swing the vibration sensing ball 30 together with the first agitator 21 and the second agitator 25 of the agitation means 20.

Meanwhile, a supply speed of the injection solution may be controlled through the opening degree of the air inlet/outlet hole 57*c* by using the air adjustment cap 59 fastened to the slit adapter 57. Finally, the flow rate of the injection solution to be injected into the person who receives the injection solution via the liquid drop tube 71 of the guide tube 70, the extension tube 73, and the injection needle 72 may be controlled through the injection flow rate controller 74.

Accordingly, the medical injection device 1 of the present embodiment may freely control the level and the injection rate of the injection solution filled in the container and the filter through the injection solution level controller 50 by connecting the container 10 and the injection solution filter 40 with each other. In particular, the injection solution may be injected while maintaining a state in which the inside of the injection solution filter 40 is a completely filled with the injection solution, such that the injection solution filter 40 is subjected to the sediment filtration process therein. Thereby, the target substance such as stem cells may be stably filtered and injected without damage due to the injection solution filter medium 45.

Hereinafter, a medical injection device 1 according to other embodiments of the present invention will be described with reference to the accompanying drawings. The same and similar components as those of the above-described first embodiment are denoted by the same reference numerals, and will not be repeatably described.

FIG. 10 is a perspective view illustrating a medical injection device according to a second embodiment of the present invention, and FIG. 11 is an enlarged front cross-sectional view illustrating an expansion tube of FIG. 8.

Referring to FIGS. 10 and 11, in comparison with the first embodiment, a medical injection device 200 of the present embodiment further includes an expansion tube 130 which connects the container 10 with the injection solution filter 40, and has the vibration sensing ball 30 installed therein.

Herein, the expansion tube 130 includes a ball housing space 135 formed therein for housing the vibration sensing ball 30 at the center thereof, an expansion tube inlet port 131 formed at an upper side thereof to which the injection solution outlet tube 19 is inserted and connected, and an expansion tube outlet port 132 connected to the filter inlet port 42 of the injection solution filter 40. The expansion tube has an enlarged cross-sectional area of an internal flow passage at a center portion in a longitudinal direction thereof.

Therefore, when applying an external force to the container 10 to agitate the injection solution then vibration occurs, the vibration is transmitted to the expansion tube 130 through the injection solution outlet port 19, and the vibration sensing ball 30 housed in the ball housing space 135 swings, thereby repeatably opening/closing the expansion tube outlet port 132, that is, a lower injection solution flow passage connected to the injection solution filter.

As such, the vibration sensing ball 30, which has been housed in the lower cross-section reduced portion of the container 10 in the first embodiment, is housed and installed in the separate expansion tube 130, such that a residence time of the injection solution in the lower cross-section reduced portion of the container 10 is extended, and the concentration of the stem cells is increased, and thereby a lot of solidification phenomenon may be prevented from occurring. In addition, the second agitator 25 of the agitation means 20 extends to the lower end of the cross-section reduced portion of the container 10, thereby further enhancing the agitation effect of the injection solution.

In addition, the vibration sensing ball 30 installed in the expansion tube 130 is connected to the lower connecting ring 27 of the second agitator 25 of the agitation means 20 provided in the container 10 through the connecting line 31 so as to move in conjunction therewith. Therefore, when fully filling the expansion tube 130 with the injection solution, even if an external vibration is transmitted, there is a limitation in the opening/closing operation of the vibration sensing ball 30 in the first embodiment. However, in response to the movement of the agitation means 20 through the connecting line 31, the movement of the vibration sensing ball 30 is increased, and thereby, the opening/closing operation of the expansion tube outlet port 132 may be more smoothly induced.

Meanwhile, in the medical injection device 200 of the present embodiment, except that, the injection solution flows into the expansion tube 130 through the injection solution outlet port 19 of the container 10 in an initial stage of injecting the injection solution through the injection solution inlet port 16 of the container 10, and fills the inside of the expansion tube 130 whose expansion tube outlet port 132 is closed by the vibration sensing ball 30 to come up to a level inside the container 10, it is possible to control the level of the injection solution filled in the container 10 and the filter 40 through the injection solution level controller 50 via the same process as that described in FIG. 9, and thereby controlling the injection rate of the injection solution.

FIG. 12 is a perspective view illustrating a medical injection device according to a third embodiment of the present invention, and FIG. 13 is a front cross-sectional view illustrating the injection solution level controller of FIG. 10.

Referring to FIGS. 12 and 13, a medical injection device 200 of the present embodiment is different from the second embodiment in that a third level control port 133 is formed at an upper portion of an expansion tube 130 in which the vibration sensing ball 30 is housed. The third level control port 133 of the expansion tube 130 is connected to the first level control port 18 of the container 10 and the second level control port 44 of the injection solution filter 40 by the injection solution level controller 250. Therefore, it is possible to control the injection rate of the injected injection solution, as well as control the level of the injection solution filled in each component through the injection solution level controller.

Accordingly, a branched connection tube 251 of the injection solution level controller 250 of the present embodiment includes a branched tube 252, from which a second branched tube part is branched and extended, for connecting a connection tube part that connects the first level control port 18 and the slit adapter 57, which is coupled to an upper open end portion of the branched connection tube, with the third level control port 133 together with the above-described second level control port 44. The air adjustment cap is fastened to an air inlet slit forming end of the slit adapter to adjust an opening degree of the air inlet slit.

In addition, as described above, a first connection tube 253 connects a first branch end portion of the second branched tube part of the branched tube 252 with the second level control port 44 of the injection solution filter 40, and a second connection tube 255 connects a second branch end portion of the second branched tube part of the branched tube 252 with the third level control port 133 of the expansion tube 130.

Further, the second connection tube 255 is made of a flexible material similar to the above-described first connection tube 253, and controls the cross-sectional area of the internal flow passage of the second connection tube 255 through a second connection tube clamp 256, such that air trapped in the expansion tube 130 may be more freely discharged to the outside, or outside air may be introduced into the expansion tube 130 through the second connection tube 255.

Accordingly, in the present embodiment, similar to the above-described container 10 and the injection solution filter 40, the level of the injection solution filled in the expansion tube 130 and the injection rate of the injection solution may be more freely controlled using the second connection tube 255 of the injection solution level controller 250.

FIG. 14 is a front cross-sectional view illustrating a medical injection device according to a fourth embodiment of the present invention, FIG. 15 is a plan view illustrating a middle fixing bar of FIG. 14, and FIGS. 16(a) to 16(c) are plan views illustrating respective modifications for the middle fixing bar of FIG. 15.

Referring to FIGS. 14 and 15, a medical injection device 1 of the present embodiment further includes a hanger 400 for movably hanging and fixing the container 10.

The hanger 400 includes a lower pedestal 410, a vertical support 420, and a middle fixing bar 440.

Herein, similar to the well-known conventional hanger, the vertical support 420 of the hanger 400 is vertically extended from the lower pedestal 410 having wheels 411. The vertical support 420 has an upper hanger part 430 formed at an upper end thereof in a bent shape so that the container 10 of the medical injection device 1 may be hung and fixed using the above-described latch 17.

However, compared to the well-known conventional hanger, the hanger of the present embodiment is characterized by further including the middle fixing bar 440 which is horizontally installed on the vertical support 420 and is capable of gripping and fixing the lower side of the corrugated portion of the bellows connector 60.

Herein, as an example, the middle fixing bar 440 includes a straight horizontal support part 441, a support fixing part 442 and a bellows connector fixing part 445, which are formed at opposite ends thereof.

The support fixing part 442 includes a fixing ring which is vertically movably fitted on the vertical support 420, and a fastening screw 443 which is installed through one side of the fixing ring. Therefore, a fixed height of the bellows connector 60 may be freely adjusted in the vertical direction of the vertical support 420.

In addition, the bellows connector fixing part 445 is formed in a circular clip shape so as to surround and fix the lower portion of the bellows connector 60, from which the connection part of the liquid drop tube 71 of the guide tube 70 extends. That is, the bellows connector fixing part 445 has a fixed side semicircular portion fixed to one end of the horizontal support part, and an open side semicircular portion whose one end is hinged to the fixed side semicircular portion and the other end is separately coupled to the fixed side semicircular portion, and the lower end portion of the bellows connector 60 is inserted and fixed between the semicircular portions.

In the present embodiment, as an example, the middle fixing bar 440 is described having a configuration in which the horizontal support part 441 extends in a form of a straight-line bar, but the present invention is not limited thereto. Of course, as illustrated in FIG. 16, the middle fixing bar may have a variety of shapes, including triangular, square, or circular, so as to serve as a handle or perform additional desired purposes of grasping medical instruments.

Of course, a vibrating device may be additionally provided between the upper hanger part 430 of the vertical support 420 and the intermediate fixing table 440 so as to connect the container 10 and transmit vibration for agitating the injection solution.

Figure 17B:
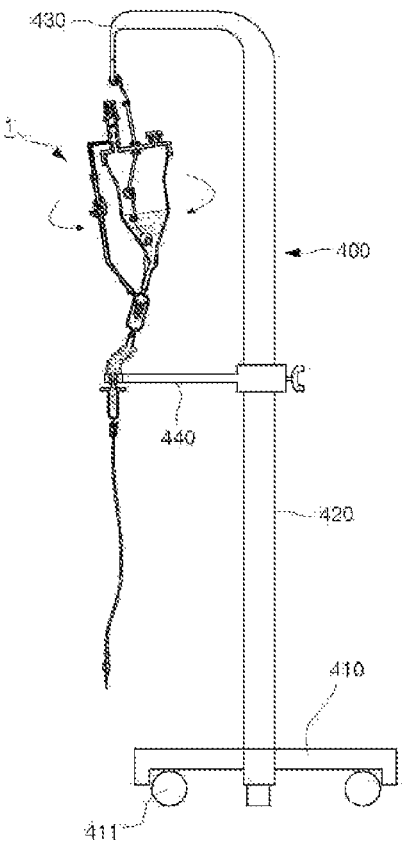

FIG. 17 is front cross-sectional views illustrating states of vibrating the medical injection device to agitate the injection solution using the hanger of FIG. 14.

Referring to FIG. 17, after the container 10 is hung and fixed to the upper hanger part 430 of the vertical support 420 so as to freely move within a limited range, the lower portion of the bellows connector 60 is grasped and fixed using the middle fixing bar 440, such that the injection device 1 is attached to the fixing table 400.

Then, as described above in FIG. 9, the injection solution filter 40 is adjusted so as to fill the injection solution at a preset level, and then the container 10 is vibrated manually or using the above-described vibrating device, such that the injection solution may be continuously agitated and injected.

At this time, by holding the lower portion of the bellows connector 60 using the middle fixing bar 440, sufficient vibration is applied to the upstream side from the bellows connector 60 including the container 10, thereby enhancing the agitation effect of the injection solution. In this process, by preventing the applied vibration from being transmitted to the downstream side of the bellows connector 60, the injection solution may be more safely injected.

While the present invention has been described with reference to the preferred embodiments, the present invention is not limited to the above-described specific embodiments, and it will be understood by those skilled in the art that various modifications and variations may be made within the detailed description of the invention and accompanying drawings without departing from the scope of the present invention as defined by the appended claims, as well as these modifications and variations should be included in the scope of the present invention.

DESCRIPTION OF REFERENCE NUMERALS 1, 100, 200: Medical injection device,
10: Container
11: Container body,
12: Internal storage space
15: Container cover,
15a: Upper fixing ring
15b: Lower fixing ring,
16: Injection solution inlet port
16a: Protection wall,
16b: Inlet port cap
17: Latch,
18: First level control port
19: Injection solution outlet port,
20: Agitation means
21: First agitator,
22: Upper connecting ring
23: Lower connecting ring,
25: Second agitator
26: Upper connecting ring,
27: Lower connecting ring
30: Vibration sensing ball,
31: Connecting line
40: Injection solution filter,
41: Filter housing
42: Filter inlet port,
43: Filter outlet port
44: Second level control port,
45: Injection solution filter medium
50, 250: Injection solution level controller,
51, 251: Branched connection tube
52, 252: Branched tube,
52a: Connection tube part
52b: First branched tube part,
53, 253: First connection tube
54, 254: First connection tube clamp,
55: Air filter
55a: Filter housing,
56: Air filter medium
57: Slit adapter,
57a: Branched tube connection part
57b: Cap fastening part,
57c: Air inlet/outlet hole
58: Open slit,
59: Air adjustment cap
59a: Cap body,
59b: Opening/closing protrusion
60: Bellows connector,
70: Guide tube
71: Liquid drop tube,
72: Injection needle
73: Extension tube,
74: Injection flow rate controller
130: Expansion tube,
131: Expansion tube inlet port
132: Expansion tube outlet port,
133: Third level control port
135: Ball housing space,
255: Second connection tube
256: Second connection tube clamp,
400: Hanger
410: Lower pedestal,
411: Wheel
420: Vertical support,
430: Upper hanger part
440: Middle fixing bar,
441: Horizontal support part
442: Support fixing part,
445: Bellows connector fixing part

The invention claimed is:

1. A medical injection device comprising:
a container including an internal storage space formed therein to contain and store an injection solution, and an injection solution outlet port formed at a lower portion thereof;
an injection solution filter connected to the injection solution outlet port of the container to filter out the injection solution flown through the injection solution outlet port;
a guide tube connected to a lower portion of the injection solution filter to provide a flow passage for injecting the injection solution filtered through and discharged out of the injection solution filter;
an injection solution level controller which is configured to control an opening degree for allowing an air to be flown into or discharged from the container, and connects a first level control port formed at an upper portion of the container and a second level control port formed at an upper portion of the injection solution filter in communication with each other; and
an agitation means which is provided in the container, and when vibration occurs in the container, is configured to swing to agitate the injection solution in the container,
wherein the agitation means comprises:
a first agitator suspended and fixed to an upper side of the container so as to move without hindrance and
a second agitator connected to a lower end of the first agitator so as to move without hindrance,
wherein the first agitator is formed in such a way that a lower portion of the first agitator is heavier than an upper portion of the first agitator, and the second agitator is formed in such a way that an upper portion of the second agitator is heavier than a lower portion of the second agitator.

2. The medical injection device according to claim 1, wherein the injection solution level controller comprises:
a branched connection tube which connects the first level control port with the second level control port;
a slit adapter which is connected to the branched connection tube and has a slit-shaped air inlet/outlet hole formed therein; and an air adjustment cap coupled to the slit adapter to control an opening degree of the air inlet/outlet hole.

3. The medical injection device according to claim 2, wherein the branched connection tube comprises:
a branched tube having a first branched tube part formed extending from a connection tube part which connects the first level control port with the slit adapter; and
a first connection tube which connects the first branched tube part of the branched tube with the second level control port of the injection solution filter.

4. The medical injection device according to claim 3, wherein the first connection tube is made of a flexible material, and comprises:
a first connection tube clamp provided on an outer circumference of the first connection tube to press the first connection tube so as to control a size of a cross-sectional area of an internal flow passage defined therein.

5. The medical injection device according to claim 2, further comprising an air filter located between the slit adapter and the branched connection tube,
wherein the air filter comprises:
a filter housing having an internal filtration space formed therein; and
an air filter medium installed in the filter housing to filter air flowing through the air inlet/outlet hole.

6. The medical injection device according to claim 5, wherein the slit adapter is formed integrally with the air filter.

7. The medical injection device according to claim 1, wherein the first agitator has upper and lower connecting rings which are formed by bending upper and lower end portions of a rod in a spiral shape and the second agitator has upper and lower connecting rings which are formed by bending upper and lower end portions of a rod in a spiral shape,
the upper connecting ring of the second agitator is hooked to the lower connecting ring of the first agitator,
wherein the first agitator is formed in such a way that the lower connecting ring of the first agitator is larger than the upper connecting ring of the first agitator, and the second agitator is formed in such a way that the upper connecting ring of the second agitator is larger than the lower connecting ring of the second agitator.

8. The medical injection device according to claim 1, wherein the container is formed so as to have a cross-sectional reduced portion whose lower portion is reduced toward the injection solution outlet port, and
the container further comprises a vibration sensing ball housed in the cross-sectional reduced portion to open and close the injection solution outlet port according to the vibration applied to the container.

9. The medical injection device according to claim 8, wherein the vibration sensing ball is connected to a lower end portion of the agitation means through a connecting line so as to move in conjunction with the agitation means.

10. The medical injection device according to claim 8, wherein the vibration sensing ball has a lower portion with a weight larger than that of an upper portion thereof, and at least the lower portion is formed as a curved portion so as to close the injection solution outlet port.

11. The medical injection device according to claim 10, further comprising a bellows connector which connects the injection solution filter with the guide tube, and is made of an elastic material.

12. The medical injection device according to claim 11, further comprising a hanger configured to movably hang and fix the container.

13. The medical injection device according to claim 12, wherein the hanger further comprises a middle fixing bar configured to grasp and fix a lower portion of the bellows connector.

14. The medical injection device according to claim 13, wherein the middle fixing bar is formed in a shape of a straight line, a circle, an ellipse or a polygon shape.

15. The medical injection device according to claim 1, further comprising:
an expansion tube which connects the container with the injection solution filter; and
a vibration sensing ball housed in the expansion tube to open and close a lower injection solution flow passage connected to the injection solution filter according to a vibration applied to the container, and
wherein the expansion tube has an enlarged cross-sectional area of an internal flow passage at a center portion of the expansion tube along the longitudinal direction from the container towards the injection solution filter.

16. The medical injection device according to claim 15, wherein the expansion tube further comprises a third level control port formed at an upper portion thereof, to which the injection solution level controller is connected.

17. The medical injection device according to claim 16, wherein the injection solution level controller comprises:
a branched connection tube which is branched so as to connect the first level control port and the second level control port, and to connect the first level control port and the third level control port, respectively;
a slit adapter coupled to an upper open end portion of the branched connection tube; and
an air adjustment cap which is fastened to an air inlet slit forming end of the slit adapter to adjust an opening degree of the air inlet slit.

18. The medical injection device according to claim 17, wherein the branched connection tube comprises:
a branched tube having a first branched tube part formed extending from a connection tube part which connects the first level control port with the slit adapter;
a first connection tube which connects the first branched tube part with the second level control port of the injection solution filter; and
a second connection tube which connects the first branched tube part with the third level control port.

19. The medical injection device according to claim 18, wherein the first connection tube and the second connection tube are made of a flexible material, and respectively comprises:
a first connection tube clamp provided on an outer circumference of the first connection tube so as to control a cross-sectional area of an internal flow passage of the first connection tube; and
a second connection tube clamp provided on an outer circumference of the second connection tube so as to control the cross-sectional area of the internal flow passage of the second connection tube.

20. The medical injection device according to claim 15, wherein the vibration sensing ball is connected to a lower portion of the agitation means inside the container through a connecting line so as to move in conjunction with the agitation means.

21. The medical injection device according to claim 15, wherein the vibration sensing ball has a lower portion with a weight larger than that of an upper portion thereof, and the lower portion is formed as a curved portion so as to close the lower injection solution flow passage.

* * * * *